(12) United States Patent
Wold et al.

(10) Patent No.: US 10,458,938 B2
(45) Date of Patent: Oct. 29, 2019

(54) SYSTEM AND METHOD FOR MONITORING OF FLOOR CONDITIONS

(71) Applicant: Ecolab USA Inc., St. Paul, MN (US)

(72) Inventors: Andrew S. Wold, Bloomington, MN (US); Robert D. Hei, Baldwin, WI (US); Catherine F. Hanson, Hastings, MN (US); Ryan J. Drake, White Bear Lake, MN (US); Ramakrishnan Balsubramanian, Stillwater, MN (US)

(73) Assignee: Ecolab USA Inc., St. Paul, MN (US)

( * ) Notice: Subject to any disclaimer, the term of this patent is extended or adjusted under 35 U.S.C. 154(b) by 1082 days.

(21) Appl. No.: 13/828,719

(22) Filed: Mar. 14, 2013

(65) Prior Publication Data

US 2014/0278252 A1     Sep. 18, 2014

(51) Int. Cl.
   *G05D 1/02*   (2006.01)
   *G01N 21/94*  (2006.01)
   *G01N 27/04*  (2006.01)

(52) U.S. Cl.
   CPC .......... *G01N 27/048* (2013.01); *G05D 1/0219* (2013.01); *G01N 21/94* (2013.01)

(58) Field of Classification Search
   CPC ....... A47L 5/14; G05D 1/0219; G01N 27/048
   USPC ....... 702/104, 134, 150, 175, 180, 184, 189; 15/319; 318/568.12; 340/521
   See application file for complete search history.

(56) References Cited

U.S. PATENT DOCUMENTS

| | | | |
|---|---|---|---|
| 4,369,543 A | 1/1983 | Chen et al. | |
| 5,279,672 A | 1/1994 | Betker et al. | |
| 5,446,445 A * | 8/1995 | Bloomfield | G08B 17/10 340/521 |
| 5,995,884 A | 11/1999 | Allen et al. | |
| 6,208,272 B1 | 3/2001 | Henry | |
| 6,446,302 B1 | 9/2002 | Kasper et al. | |
| 6,457,206 B1 | 10/2002 | Judson | |
| 6,594,844 B2 | 7/2003 | Jones | |
| 6,763,282 B2 | 7/2004 | Glenn et al. | |
| 7,320,149 B1 | 1/2008 | Huffman et al. | |
| 7,459,871 B2 | 12/2008 | Landry et al. | |
| 7,837,958 B2 | 11/2010 | Crapser et al. | |

(Continued)

FOREIGN PATENT DOCUMENTS

| | | |
|---|---|---|
| DE | 19614916 A1 | 11/1997 |
| GB | 2313190 A | 11/1997 |
| KR | 950008437 B1 | 7/1995 |

OTHER PUBLICATIONS

International Search Report and Written Opinion of counterpart international application No. PCT/US2014/021237, dated Jun. 17, 2014, 11 pp.

*Primary Examiner* — Eman A Alkafawi
(74) *Attorney, Agent, or Firm* — Shumaker & Sieffert, P.A.

(57) ABSTRACT

A floor monitoring device monitors the condition of various flooring substrates. The floor monitoring device may traverse a route through an environment and collect data concerning the condition of the floor. The device may also communicate the floor condition data to another computing device. In some examples, the floor monitoring device may analyze the floor condition data and identify any notable floor conditions within the monitored environment. Alternatively or in addition, the computing device may analyze the floor condition data and identify and/or address notable floor conditions within the monitored environment.

20 Claims, 5 Drawing Sheets

(56) References Cited

U.S. PATENT DOCUMENTS

| | | | |
|---|---|---|---|
| 7,873,437 B2 | 1/2011 | Aldred et al. | |
| 7,885,738 B2 | 2/2011 | Park et al. | |
| 8,248,256 B1* | 8/2012 | Gerardi | G08B 21/20 340/604 |
| 8,386,081 B2* | 2/2013 | Landry | G05D 1/0272 318/568.12 |
| 8,387,193 B2* | 3/2013 | Ziegler | A47L 5/14 15/319 |
| 8,545,635 B1* | 10/2013 | Azevedo | C11D 3/386 134/26 |
| 2003/0030398 A1 | 2/2003 | Jacobs et al. | |
| 2005/0065662 A1* | 3/2005 | Reindle | A47L 9/2821 701/1 |
| 2005/0195296 A1* | 9/2005 | Compton | H04N 5/3651 348/243 |
| 2006/0103523 A1* | 5/2006 | Field | A47L 11/4011 340/540 |
| 2010/0235037 A1 | 9/2010 | Vian et al. | |
| 2011/0004342 A1* | 1/2011 | Knopow | A47L 5/28 700/253 |
| 2011/0316695 A1* | 12/2011 | Li | G01S 5/02 340/539.13 |
| 2012/0075464 A1 | 3/2012 | Derenne et al. | |
| 2012/0116803 A1 | 5/2012 | Reid et al. | |
| 2014/0124004 A1* | 5/2014 | Rosenstein | A47L 9/2852 134/18 |
| 2015/0006016 A1* | 1/2015 | Friedman | A47L 9/009 701/26 |

* cited by examiner

SYSTEM AND METHOD FOR MONITORING OF FLOOR CONDITIONS

TECHNICAL FIELD

The disclosure relates to devices that monitor floor conditions.

BACKGROUND

In many industrial and commercial businesses, cleaning and maintenance of the floors is an ongoing endeavor. Grocery stores, food production facilities, commercial kitchens, commercial laundry facilities, hotels, restaurants, office buildings, public restrooms, etc. are examples of facilities in which the upkeep of the floor is a continuing occupation. The presence of spills, dirt, or other floor conditions can affect the safety of persons in the area, contribute to an unsightly environment, and/or increase wear and tear on the floor itself.

SUMMARY

In general, the disclosure is directed to floor monitoring devices that monitor the condition of flooring substrates. The floor monitoring device may traverse a route around an environment and collect data concerning the condition of the floor. The device may communicate the floor condition data to a base station, a local computer, or other computing device. In some examples, the floor monitoring device may analyze the floor condition data and identify any notable floor conditions within the monitored environment. In other examples, the base station may analyze the floor condition data and identify and/or address notable floor conditions within the monitored environment.

In one example, the disclosure is directed to a system comprising a floor monitoring device including one or more floor condition sensors that collect floor condition data associated with an environment to be monitored, and a computing device that receives the collected floor condition data from the floor monitoring device, the computing device including an analysis module that analyzes the received floor condition data to identify notable floor conditions within the environment to be monitored and a reporting module that generates one or more reports concerning the received floor condition data. The one or more floor condition sensors may include at least one of a colorimeter, an imaging device, a photocell, a reflectometer, a conductivity sensor, a thickness gauge, a moisture sensor, a salt sensor, an ultrasonic sensor, or an optical sensor. The collected floor condition data may includes data concerning one or more of a gloss, a film thickness, a distinctness of image (DOI), a color, a surface profile, a coefficient of friction, an image, a moisture level, a salt content, or a soil level. The floor monitoring device may store one or more maps corresponding to routes within the environment to be traversed by the floor monitoring device. The floor monitoring device may be associated with an apparatus or accessory device, and the one or more floor condition sensors may collect the floor condition data as the associated apparatus is moved around the environment to be monitored.

In another example, the disclosure is directed to a device comprising one or more floor condition sensors that collect floor condition data associated with an environment to be monitored, and a controller that receives the collected floor condition data from the one or more floor condition sensors, analyzes the received floor condition data to identify notable floor conditions within the environment to be monitored, and generates one or more reports concerning the received floor condition data.

In another example, the disclosure is directed to a method comprising receiving, from one or more floor condition sensors, floor condition data associated with an environment to be monitored, analyzing, with a computing device, the received floor condition data to identify any notable floor conditions within the environment to be monitored, and generating, with a computing device, one or more reports concerning the received floor condition data. The method may include receiving additional floor condition data concerning an area within the environment associated with an identified notable floor condition subsequent to the identified notable floor conditions being addressed and analyzing the additional floor condition data to determine whether or not the notable floor condition was adequately addressed. The method may further include generating a report concerning how the notable floor condition was addressed.

The details of one or more examples are set forth in the accompanying drawings and the description below. Other features and advantages of the invention will be apparent from the description and drawings, and from the claims.

DETAILED DESCRIPTION

Figure 1:
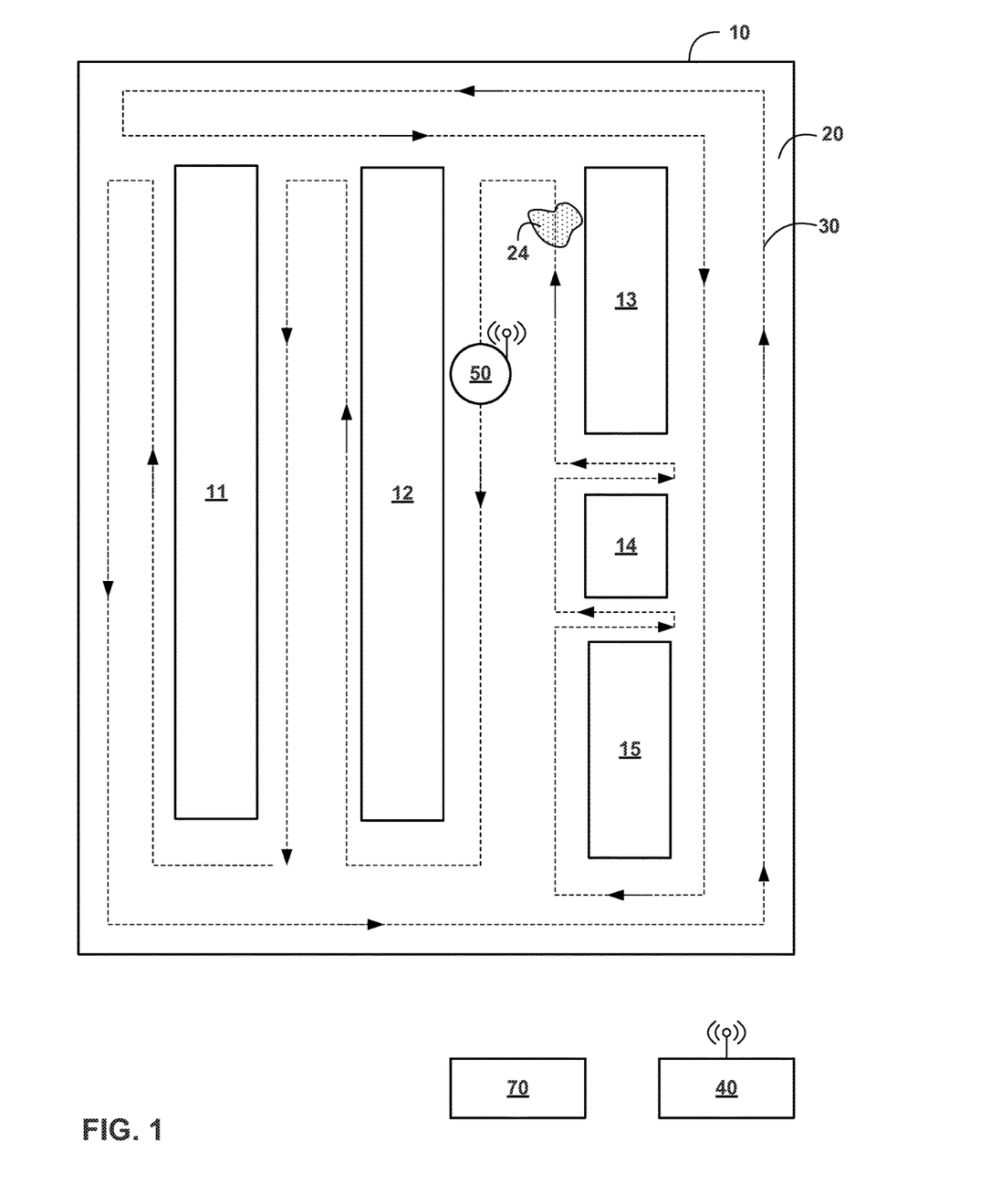
FIG. 1 is a diagram illustrating an example floor monitoring device in an environment in which the condition of the floor is to be monitored.

FIG. 1 is a block diagram illustrating an example floor monitoring device 50 in an environment 10 in which the condition of the floor is to be monitored. In this example, device 50 is capable of monitoring the condition of various flooring substrates. Flooring substrates that may be monitored may include hard flooring, such as vinyl, ceramic or porcelain tile, terrazzo, marble, granite, concrete, wood, laminate, etc.; carpet or rugs; rubber or epoxy flooring; and others. Example floor condition data collected by floor monitoring device 50 may include, but is not limited to, gloss, film thickness, distinctness of image (DOI), color, surface profile, coefficient of friction, images, moisture levels, salt content, soil content, etc.

In general, floor monitoring device 50 traverses the environment and monitors floor conditions throughout the environment. There are several ways in which the floor monitoring device may traverse the environment.

In the example shown in FIG. 1, device 50 follows an example predetermined route 30 around the environment. Route 30 may be designed such that device 50 monitors desired areas of the floor. To that end, device 50 may include one or more preprogrammed maps corresponding to one or more routes (such as route 30) over which device 50 may traverse the environment. The preprogrammed map or maps may then be used during a working phase during which device 50 follows the preprogrammed route around the environment and collects data regarding the condition of the floor. The map or maps may be designed such that substantially all of the free surface of the floor in the environment is monitored as device 50 traverses the corresponding route. Alternatively, one or more of the maps may be designed such that only certain areas of the floor are monitored. As another alternative, device 50 may include a plurality of maps, each corresponding to a route through one of a corresponding plurality of areas within the environment.

In another example, device 50 may include a training phase during which device 50 is manually guided through one or more desired routes around the environment. Device 50 may store maps of these routes to be used during subsequent working phases. In another example, device 50 may be capable of exploring the environment during a training or learning phase and generating one or more maps to be used during subsequent working phases. In other examples, device 50 may follow a predetermined path marked by, for example, a wire or cable buried beneath the floor, beacons positioned at various locations throughout the environment, or other mechanism for guiding device 50 around the environment. Thus, although FIG. 1 shows a specific environment and a specific route over which device 50 traverses the environment, it shall be understood that many other environments and routes are possible, and that the disclosure is not limited in this respect.

In another example, device 50 need not be self-propelling or self-guided, but may be associated with and transported around the environment by another apparatus or accessory device 70. For example, device 50 may be associated with and moved around the environment by a floor cleaning machine, an auto scrubber, a mop bucket, a floor finish applicator, a forklift or other piece of industrial machinery, a pallet truck, a laundry cart, a housekeeping cart, a shopping cart, or other apparatus that may move or is moved around an environment. Device 50 may be mounted to, connected to, carried by or otherwise associated with the other apparatus or accessory device 70.

In another example, the accessory device 70 may respond to notable floor conditions detected by floor monitoring device 50. For example, if a spill is detected, accessory device 70 may include a floor cleaning machine configured to address spills. If a worn coating is detected, accessory device 70 may include a floor finish applicator configured to apply a coating to the floor.

Referring again to FIG. 1, environment 10 includes a floor 20 and one or more obstacles indicated here by reference numerals 11, 12, 13, 14, and 15. As floor monitoring device 50 follows route 30 around environment 10, one or more floor condition sensors collect data concerning the condition of the floor. In this example, route 30 is designed such that device 50 travels around obstacles 11-15 and is able to collect floor condition data concerning substantially all of the free area of floor 20. In other examples, device 50 may store one or more maps corresponding to routes covering small areas of the floor within environment 10. In other examples, device 50 may be carried or transported by an associated device or apparatus. However, example route 30 shown in FIG. 1 will be used for purposes of illustration.

Device 50 may further include a wireless transmitter/receiver that permits communication between device 30 and one or more computing devices, indicated generally by reference numeral 40. As device 50 traverses route 30, the one or more of the floor condition sensors on device 50 may collect data concerning the condition of floor 20. Location data, as well as time and date information, associated with the collected floor condition data may also be stored and/or communicated by device 50. The floor condition data may be collected at predetermined sampling rate(s) sufficient to detect notable floor conditions along route 30.

In examples, device 50 may also periodically transmit the collected floor condition data to computing device 40. Computing device(s) 40 may include, for example, one or more of a base station or docking station associated with the environment 10. Computing device 40 may also include a personal or laptop computer, a personal digital assistant (PDA), a tablet computer, a cell phone, or other type of electronic device capable of wired or wireless communication.

Device 50 may transmit the floor condition data to one or more computing devices 40 via any type of wireless technology including Wi-Fi, Bluetooth, Near Field Communication (NFC), Radio Frequency (RF), satellite, cellular network, etc. In another example, device 50 may transmit the floor condition data to one or more computing devices 40 via a physical connection, such as when computing device provides a docking station, or when a physical connector such as a USB connector, ethernet cable, or other physical connector is used to connect device 50 with a computing device 40.

In some examples, the collected floor condition data is communicated to computing device 40 for analysis. Computing device 40 (or some other computer or processor with which device 40 is in communication) may then analyze the received floor condition data to identify any notable floor conditions present in environment 10. In other examples, floor monitoring device 50 may include analysis capabilities by which the collected floor condition data may be analyzed to identify notable floor conditions. The location of any notable floor conditions along route 30, along with a time and date stamp, may be transmitted to computing device 40.

In another example, computing device 40 may act as a docking or charging station for one or more floor monitoring devices 50. For example, floor monitoring device 50 may include a rechargeable battery or other power source 58. Computing device 40 may include physical docking components configured to electrically connect with corresponding components of floor monitoring device 50. Computing device 40 and floor monitoring device may also dock wirelessly, such as through inductive charging circuits, or other type of wireless charging. Docking of floor monitoring device 50 computing device 40 may permit recharging of battery 58, communication of floor monitoring data between device 50 and computing device 40, and/or communication of software or firmware updates, or other types of communications.

Thresholds corresponding to various notable floor conditions may be stored in device 50, computing device 40, at a remote computing device, and/or any other suitable location. The collected floor condition data may be compared to one or more of the notable floor condition thresholds to locate any such notable floor conditions. Example notable floor conditions may include, but are not limited to, the location and type of a spill or stain. For example, thresholds concerning gloss, film thickness, distinctness of image (DOI), color, surface profile, coefficient of friction, images, moisture levels, salt content, soil content, etc., may be set up and stored for purposes of comparison. Identification of notable floor conditions, along with their corresponding location within the environment, may be provided in real time, at periodic intervals, and/or upon request.

Figure 2:
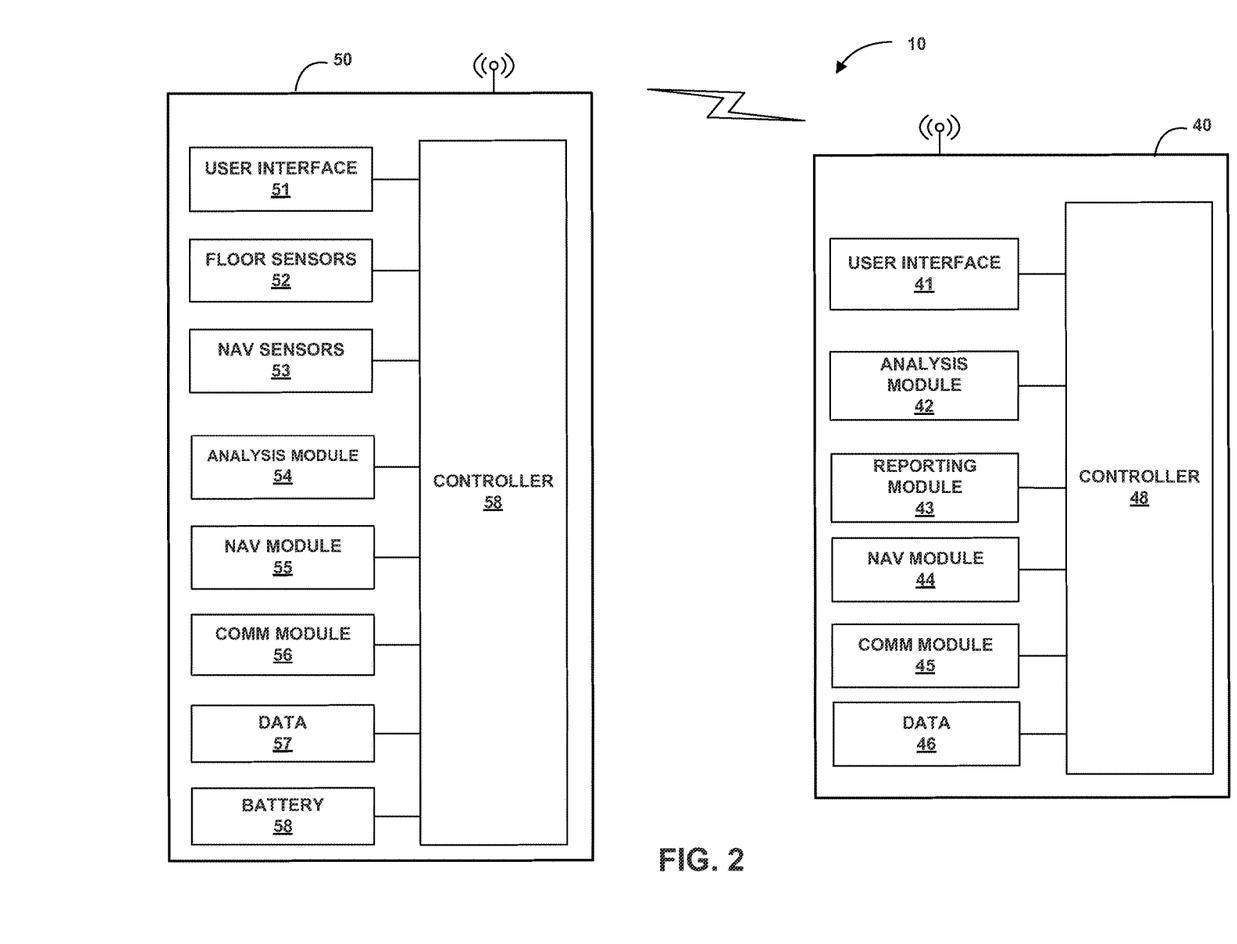
FIG. 2 is a block diagram illustrating the electronic components of an example floor monitoring device and an example base station.

FIG. 2 is a block diagram illustrating the electronic components of an example floor monitoring device 50 and an example base station 40. For purposes of illustration, example floor monitoring device 50 is self-guiding and self-propelled. However, it shall be understood that device 50 need not be capable of these functions, and need not include each and every functional block shown in FIG. 2, and the disclosure is not limited in this respect. Similarly, device 50 may include additional functional blocks not shown in FIG. 2, and the disclosure is not limited in this respect.

Example floor monitoring device 50 includes a controller 58, a user interface 51, one or more floor condition sensors 52, one or more navigational sensors 53, an optional analysis module 54, a navigation module 55, a communication module 56, and data storage 57. User interface 51 may include, for example, one or more buttons, switches, visual or audible indicators, displays, etc. by which a user may interact with device 50. Data storage 57 may include, for example, one or more maps corresponding routes over which device 50 traverses the environment to be monitored. Data storage may further include any collected floor condition data and associated location, time, and/or date information. Data storage 57 may also include baseline "clean" data corresponding to one or more flooring substate(s). Data storage 57 may also include notable floor condition data and/or thresholds corresponding to one or more flooring substate(s). Data storage 57 may also include any device settings, communication protocols, and/or any other data generated or used by device 50 during execution of its floor monitoring, analysis, or communication activities.

Controller 58 executes the various control software and programming modules by which device 50 traverses an environment and collects floor condition data. Floor condition sensors 52 may include, for example, a colorimeter, one or more imaging devices (cameras), photocells, a reflectometer, conductivity sensors, a thickness gauge, a moisture sensor, a salt sensor, an ultrasonic sensor, sensor(s) that measure the concentration of one or more chemicals in the floor finish, optical or other sensors for measuring various floor conditions such as surface roughness, coefficient of friction, color, surface profile, film thickness, or any other sensor suitable for monitoring the condition of a flooring substrate. It shall be understood that the position, location, directionality, and type of floor condition sensors 52 on device 50 may take many different forms, and that the disclosure is not limited in this respect. In examples where floor monitoring device 50 includes analysis capability, an analysis module 54, when executed by controller 58, may permit analysis of the collected floor condition data to collate or analyze the data and/or identify any notable floor conditions within the environment.

Navigational sensors 53 may include, for example, infrared, ultrasonic, optical, magnetic, pressure, or other types of sensors that permit device 50 to traverse one or more routes through the environment, and/or to sense obstacles within the environment. It shall be understood that the position, location, directionality, and type of navigation sensors 53 on device 50 may take many different forms, and that the disclosure is not limited in this respect. Navigation module 55 includes the control software that, when executed by controller 58, permits device 50 to traverse the one or more routes stored in data storage 57. Navigation module 55 may also include one or motors or other hardware that permits device 50 to move throughout the environment. Controller 58 may control the one or more motors such that device 50 traverses the route 30 indicated by the programmed map(s).

Communication module 56 provides the control software for communication between device 50 and one or more computing devices, such as computing device 40. Computing device 40 may include, for example, a controller 48, a user interface 41, an analysis module 42, a reporting module 44, a navigation module 44, a communication module 45, and data storage 46. User interface 41 may include, for example, one or more of a display, keyboard, touch screen, mouse, buttons, or other interfaces through which a user may interact with computing device 40. Data storage 46 may include, for example, any received floor condition data and associated location, time, and/or date information. Data storage 46 may also include baseline "clean" or notable floor condition data corresponding to one or more flooring substate(s) or one or more notable floor conditions. Data storage 57 may also include any device settings, communication protocols, and/or any other data generated or used by device 40 during execution of its floor monitoring, analysis, or communication activities.

Controller 48 executes the various control software and programming modules used by computing device 40 for operation of floor monitoring device 50 and/or for analysis and reporting of floor condition data received from device 50. An analysis module 42, when executed by controller 48, may permit analysis of the received floor condition data to identify any notable floor conditions within the environment. Navigation module 44 may include control software that permits computing device 40 to control the movement of floor monitoring device 40 through the environment.

Reporting module 43 may generate one or more reports presenting the raw floor condition data and/or analysis of the raw floor condition data for receipt by a user. For example, reporting module 43 may generate one or more of a text message, a page, an email, or other electronic messages or reports to be sent to a user computing device such as a cell phone, tablet computer, personal digital assistant, laptop computer, etc., upon identification of one or more notable floor conditions. Reporting module 43 may also generate one or more reports concerning the floor conditions within the environment on, for example, an hourly, daily, and/or weekly basis. Reporting module 43 may also generate one or more reports on demand in response to a user request. The types of reports generated may include tables, graphs, bar charts, text, or any other report that may help to effectively communicate the received floor condition data and/or the analysis thereof, regardless of whether notable floor conditions were detected or not.

In some examples, analysis of the floor condition data may permit either general or more specific identification of the type of notable floor condition. Depending upon the type of sensor(s) utilized and the type of notable floor condition, the system 10 may be able to identify, for example, the type of soil on the floor, the thickness of the soil on the floor, the color of the soil on the floor, etc. In some examples, the system may further identify suggested cleaning products, tools, or methods to further prepare maintenance personnel to address the notable floor condition, such as an adverse floor condition, as quickly and efficiently as possible.

To detect notable floor conditions, floor monitoring device 50 and/or computing device 40 may determine the relative degree of soil on the flooring substrate. In one example, the collected floor condition data may be compared with one or more background or baseline measurements of the flooring substrate. For example, various measurements of the flooring substrate may be made with one or more of the floor condition sensors 52 when the flooring substrate is (through objective determination) "clean." These "clean" measurements may be used as a baseline to detect notable floor conditions. For example, if the collected floor condition data does not fall within a predetermined threshold of a "clean" floor condition, a notable floor condition may be identified.

Alternatively or in addition, various measurements of the flooring substrate may be made with one or more of the floor condition sensors 52 under one or more notable floor conditions. These notable floor condition measurements may be used as a baseline to detect notable floor conditions. For example, if the collected floor condition data falls within a predetermined threshold of a notable floor condition, a corresponding notable floor condition may be identified.

The clean baseline and/or notable baseline floor conditions may be customized for the environment in which floor monitoring device is to be used. For example, floor condition data corresponding to one or more notable floor conditions expected to be encountered in a particular environment may be collected during a training or learning phase of the floor monitoring device. As another example, floor condition data corresponding to a "clean" floor within the environment to be monitored may be collected during a training or learning phase of the floor monitoring device. Customization of clean and/or notable floor conditions may permit more accurate identification of notable floor conditions, as the collected floor condition data may vary depending upon the type of flooring substrate, the type of notable floor conditions, the ambient lighting in the environment, and/or other factors.

Figure 3:
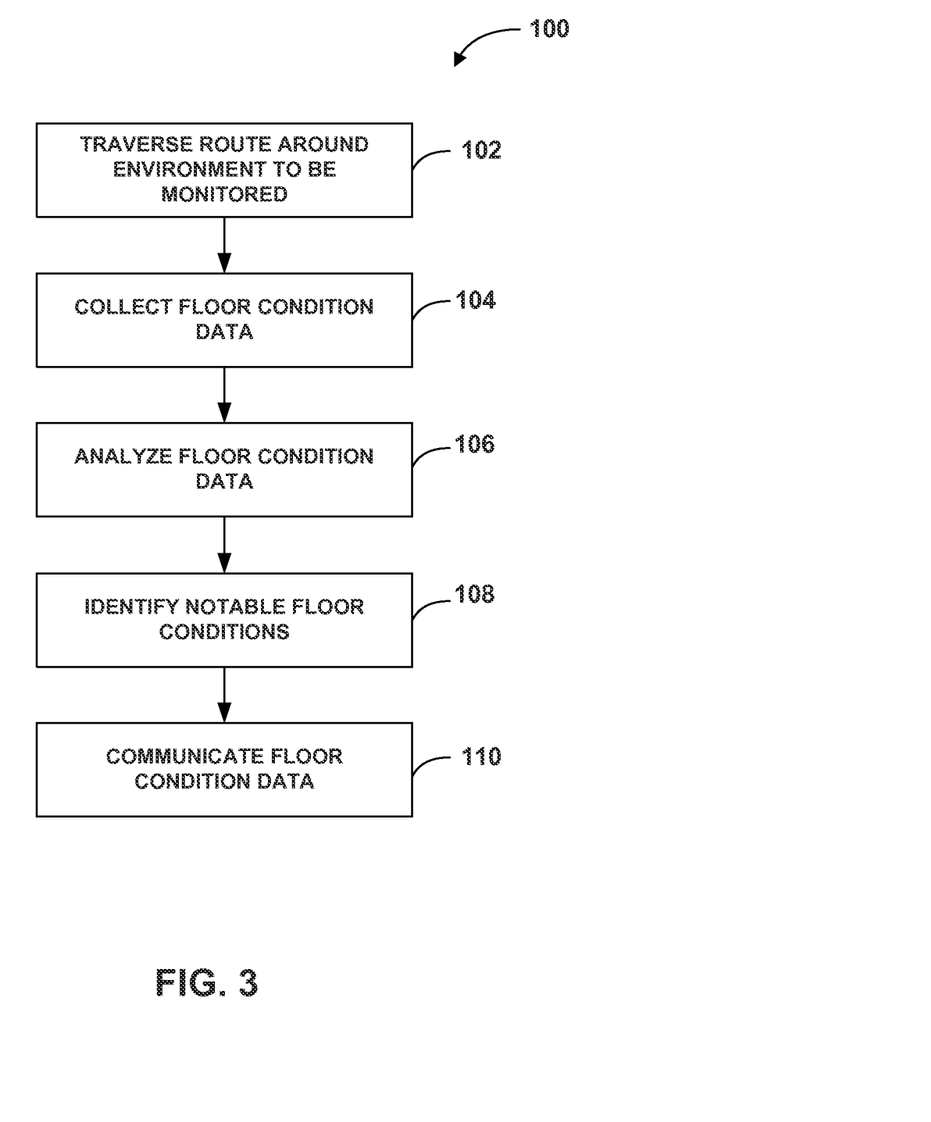
FIG. 3 is a flow chart illustrating an example process by which a floor monitoring device may traverse an environment to be monitored and collect floor condition data.

FIG. 3 is a flow chart illustrating an example process (100) by which a floor monitoring device 50 may traverse an environment to be monitored and collect floor condition data. Process (100) may be executed by, for example, a controller on board a floor monitoring device, such as controller 58 as shown in FIG. 2. The controller may cause the floor monitoring device to traverse a predetermined route in the environment to be monitored (102). In some examples, this may be accomplished using one or more maps stored on board the floor monitoring device.

The controller may manage one or more floor condition sensors to collect floor condition data (104). The floor condition data may include, for example, information concerning the relative or absolute soil level of the flooring substrate. In some examples, the floor monitoring device may include "intelligence" to identify notable floor conditions from the floor condition data (106). For example, the controller may compare the collected floor condition data with baseline floor condition data to identify any notable floor conditions within the environment (108). The baseline floor condition data may include, for example, clean baseline or notable baseline floor condition data. The controller may also periodically or upon request transmit the collected floor condition data to another computing device (110).

Figure 4:
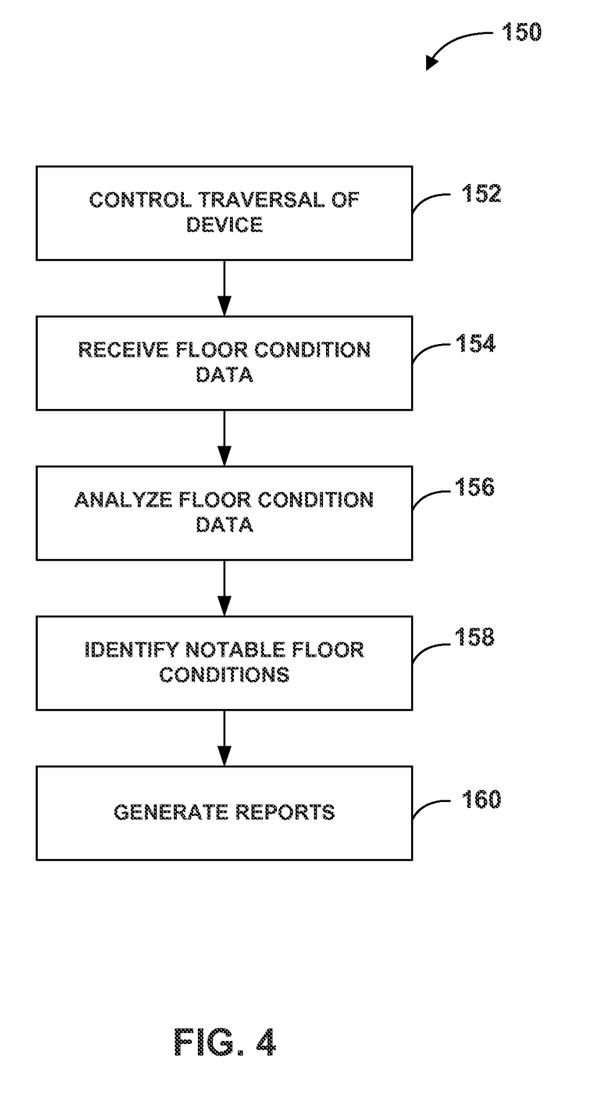
FIG. 4 is a flowchart illustrating an example process by which a computing device may analyze floor condition data received from a floor monitoring device and identify notable floor conditions within an environment to be monitored.

FIG. 4 is a flowchart illustrating an example process (150) by which a computing device may analyze floor condition data received from a floor monitoring device and identify notable floor conditions within an environment to be monitored. Process (100) may be executed by, for example, a controller of a computing device, such as controller 48 as shown in FIG. 2. In some examples, the computing device controller may manage traversal of the floor monitoring device along one or more routes within an environment to be monitored (152). In other examples, the floor monitoring device may autonomously traverse the environment. The computing device controller receives floor condition data associated with a flooring substrate within an environment to be monitored from a floor monitoring device (154). The floor condition data may be received at one or more periodic intervals or upon request. The computing device controller may analyze the floor condition data (156). For example, the controller may compare the received floor condition data with baseline floor condition data to identify any notable floor conditions within the environment (158). The baseline floor condition data may include, for example, clean baseline or notable baseline floor condition data associated with one or more flooring substrates. The computing device controller may further generate one or more reports concerning the received floor condition data or the analysis thereof (160). The report(s) may be generated at one or more periodic intervals or on demand in response to a user request. The types of reports generated may include tables, graphs, bar charts, text, or any other report that may help to effectively communicate the received floor condition data and/or the analysis thereof, regardless of whether notable floor conditions were detected or not. The reports may also or alternatively include one or more of a text message, email, or other electronic message to be sent to a user computing device such as a cell phone, tablet computer, personal digital assistant, laptop computer, etc.

Figure 5:
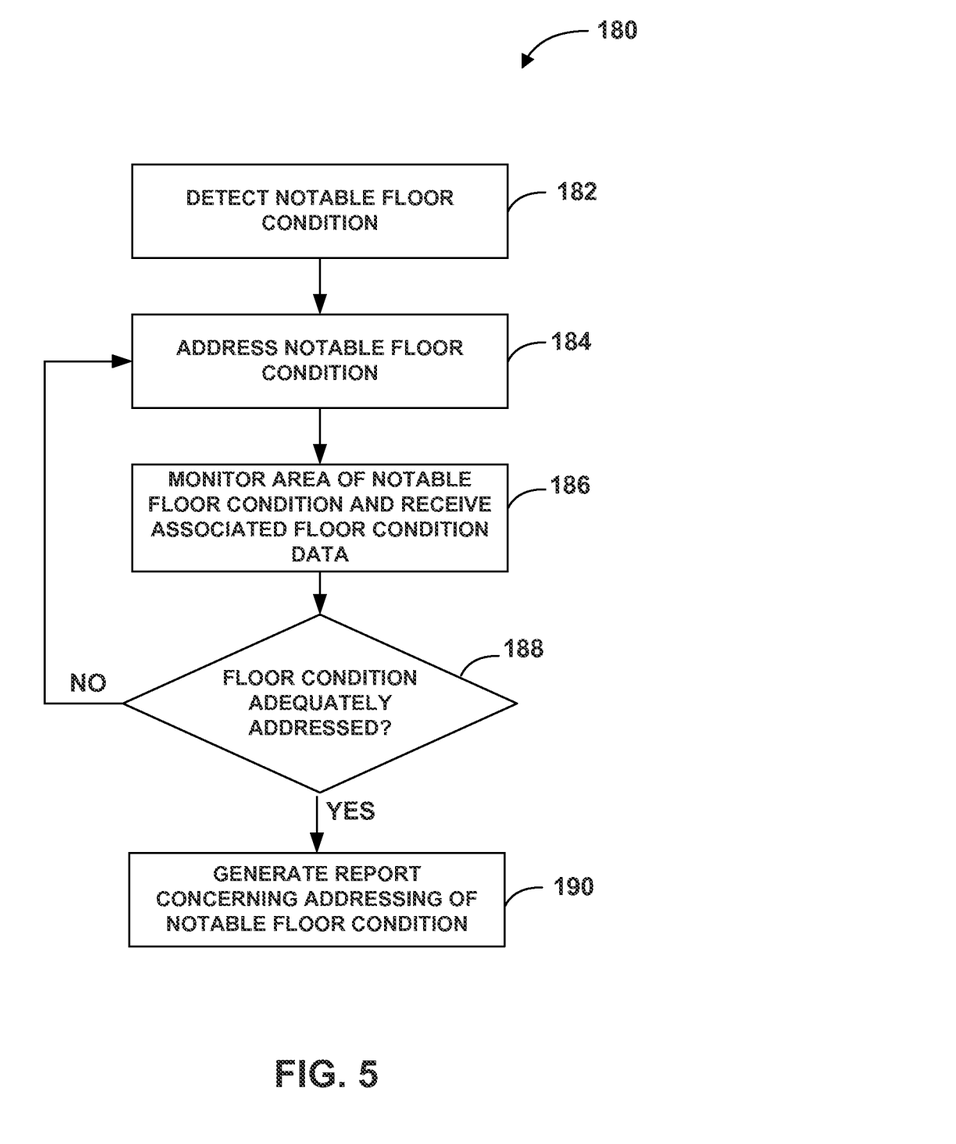
FIG. 5 is a flowchart illustrating an example process by which a computing device may determine whether detected notable floor conditions have been adequately addressed.

FIG. 5 is a flowchart illustrating an example process by which a computing device may determine whether detected notable floor conditions have been adequately addressed. If the computing device detects a notable floor condition (182), the computing device may direct the floor monitoring device or an accessory device to address the notable floor condition in an appropriate manner (184). For example, in the case of a spill, the computing device may send a command signal to the floor monitoring device or an associated or accessory device to address the notable floor condition by cleaning the area of the notable floor condition. As another example, in the case of a worn floor coating, the computing device may send a command signal to the floor monitoring device or an associated or accessory device to address the notable floor condition by applying a coating to the area of the notable floor condition. As another example, in the case of a damaged floor, the computing device may send a command signal to the floor monitoring device or an associated or accessory device to address the notable floor condition by repairing the area of the notable floor condition. Thus, it shall be understood that the notable floor conditions may be addressed using any appropriate means of addressing and/or correcting the notable floor condition.

Once the notable floor condition has been addressed, the computing device may direct the floor monitoring device to obtain additional floor condition data regarding the area of the notable floor condition (186). The computing device may then analyze the floor condition data to determine whether or not the notable floor condition was adequately addressed (188). If the computing device determines that the notable floor condition was not adequately addressed, the computing device may again instruct the floor monitoring device or other device to address the notable floor condition (184) until the notable floor condition has been adequately addressed (190). Alternatively, the computing device may cause the notable floor condition to be addressed a predetermined number of times (e.g., 1, 2, or more times) in the event that the floor condition is not adequately addressed.

If the notable floor condition has been adequately addressed or the notable floor condition has been addressed the predetermined number of times (188), the computing device may generate a report concerning the notable floor condition, how and when it was addressed, whether or not the result was satisfactory, or any other relevant analytic (190).

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a non-transitory computer-readable medium or computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term "computer-readable storage media" refers to physical storage media, and not signals or carrier waves, although the term "computer-readable media" may include transient media such as signals, in addition to physical storage media.

Various examples have been described. These and other examples are within the scope of the following claims.

The invention claimed is:

1. A system comprising:
a floor monitoring device that moves around an environment to be monitored, the floor monitoring device including one or more floor condition sensors that sense a first level of soil on a flooring substrate at each of a plurality of locations within the environment, and wherein the floor monitoring device further stores one or more maps corresponding to routes within the environment to be traversed by the floor monitoring device; and
a computing device separate from the floor monitoring device and associated with the environment that receives the first level of soil sensed at each of the plurality of location within the environment from the floor monitoring device, the computing device including:
an analysis module that, when executed by the computing device, compares the first level of soil sensed at each of the plurality of locations within the environment with baseline floor condition data representative of a clean floor condition to identify a notable floor condition within the environment, and determines a location within the environment corresponding to the notable floor condition, wherein the notable floor condition includes soil on the flooring substrate; and
a reporting module that, when executed by the computing device, generates one or more reports indicating the notable floor condition and the location within the environment corresponding to the notable floor condition,
wherein the analysis module further, when executed by the computing device, generates a command for receipt by the floor monitoring device to clean the flooring substrate at the location within the environment corresponding to the notable floor condition,
wherein the floor monitoring device moves to the location within the environment corresponding to the notable floor condition and cleans the location within the environment associated with the notable floor condition upon receipt of the command generated by the analysis module,
wherein subsequent to the floor monitoring device cleaning the flooring substrate at the location within the environment corresponding to the notable floor condition, the floor monitoring device senses a second level of soil on the flooring substrate at the location within the environment corresponding to the notable floor condition; and
wherein the analysis module further, when executed by the computing device, compares the second level of soil with the baseline floor condition data representative of a clean floor to determine whether or not the notable floor condition was adequately cleaned.

2. The system of claim 1 wherein the one or more floor condition sensors include at least one of a colorimeter, an imaging device, a photocell, a reflectometer, a conductivity sensor, a thickness gauge, a moisture sensor, a salt sensor, an ultrasonic sensor, an optical sensor, or a sensor that measures a concentration of a chemical.

3. The system of claim 1 wherein the floor condition data includes data concerning one or more of a gloss, a film thickness, a distinctness of image (DOI), a color, a surface profile, a coefficient of friction, an image, a moisture level, a salt content, or a soil level.

4. The system of claim 1 wherein the floor monitoring device further includes one or more navigation sensors that sense obstacles in a path of the floor monitoring device.

5. The system of claim 1 wherein the reporting module generates the one or more reports at periodic intervals.

6. The system of claim 1 wherein the reporting module generates the one or more reports on demand in response to a user request.

7. The system of claim 1 wherein the one or more reports include at least one of a table, a graph, a bar chart, or a text report.

8. The system of claim 1 wherein the one or more reports include at least one of a text message, a page, or an email.

9. The system of claim 1 wherein the floor monitoring device is associated with an apparatus, and wherein the apparatus comprises one of a floor cleaning machine, an auto scrubber, a mop bucket, a floor finish applicator, a forklift, a pallet truck, a laundry cart, a housekeeping cart, or a shopping cart.

10. The system of claim 1 wherein the floor monitoring device further includes a rechargeable battery, and wherein the computing device is further configured to recharge the rechargeable battery.

11. The system of claim 1 wherein the reporting module further, when executed by the computing device, generates a report concerning how the notable floor condition was addressed.

12. The system of claim 1 further including an accessory device associated with the floor monitoring device, that moves the floor monitoring device around the environment to be monitored.

13. The system of claim 10 wherein the accessory device is one of a floor cleaning machine, a mop bucket, a floor finish applicator, a laundry cart, a housekeeping cart, or a shopping cart.

14. The system of claim 10 wherein the accessory device comprises a floor cleaning device configured to address at least one of the notable floor conditions.

15. The system of claim 1 wherein the reports include identification of suggested cleaning products or tools to address the identified notable floor conditions.

16. The system of claim 1 wherein the analysis module further, when executed by the computing device, analyzes the collected floor condition data in comparison to baseline floor condition data to determine a type of soil on the floor or a color of soil in the floor.

17. The system of claim 1 wherein the computing device includes at least one of a base station, a docking station, a personal computer, a laptop computer, a personal digital assistant (PDA), a tablet computer, and a cell phone.

18. The system of claim 1 wherein the baseline floor conditions and the notable floor conditions are customized based on the environment.

19. The system of claim 1 wherein the floor monitoring device is further associated with a floor cleaning machine, and wherein the computing device further sends a command signal to the floor cleaning machine to clean the location within the environment corresponding to the identified notable floor condition.

20. A system that monitors presence of soil on a flooring substrate, comprising:

a floor monitoring device that moves around an environment to be monitored and that senses a first level of soil on the flooring substrate at each of a plurality of locations within the environment to be monitored; and a computing device that analyzes the first level of soil sensed at each of the plurality of locations to identify one or more notable floor conditions within the environment to be monitored and an associated location within the environment for each of the one or more notable floor conditions, wherein each notable floor condition is identified when the first level of soil on the flooring substrate exceeds a threshold level of soil, and wherein the computing device further generates notifications concerning the notable floor conditions, the notifications including the locations within the environment associated with each of the notable floor conditions, wherein the computing device further generates a command for receipt by the floor monitoring device to clean the flooring substrate at the locations within the environment associated with each of the notable floor conditions, wherein the floor monitoring device moves to the locations within the environment associated with the notable floor conditions and cleans the locations within the environment associated with the notable floor conditions upon receipt of the command generated by the computing device, wherein subsequent to cleaning the flooring substrate at the locations within the environment associated with the notable floor conditions, the floor monitoring device senses a second level of soil on the flooring substrate at each of the locations within the environment associated with the notable floor condition, and wherein the computing device further compares the second level of soil with the threshold level of soil to determine whether or not the identified floor condition was adequately cleaned.

* * * * *